United States Patent
Lin

(10) Patent No.: US 10,214,757 B2
(45) Date of Patent: Feb. 26, 2019

(54) PHOTOSYNTHETIC DEVICE WITH MICROFLUID CHAMBER FOR CAUSING PHOTOSYNTHESIS THEREIN AND METHOD THEREOF

(71) Applicant: Po-Kang Lin, Taipei (TW)

(72) Inventor: Po-Kang Lin, Taipei (TW)

(*) Notice: Subject to any disclaimer, the term of this patent is extended or adjusted under 35 U.S.C. 154(b) by 192 days.

(21) Appl. No.: 15/482,853

(22) Filed: Apr. 10, 2017

(65) Prior Publication Data

US 2017/0211110 A1    Jul. 27, 2017

Related U.S. Application Data

(62) Division of application No. 14/602,450, filed on Jan. 22, 2015.

(51) Int. Cl.
*C12P 19/02* (2006.01)
*C12M 1/00* (2006.01)
*C12M 3/06* (2006.01)
*C12M 1/26* (2006.01)

(52) U.S. Cl.
CPC ............ *C12P 19/02* (2013.01); *C12M 21/02* (2013.01); *C12M 23/16* (2013.01); *C12M 33/14* (2013.01)

(58) Field of Classification Search
CPC ...... C12M 21/02; C12M 23/16; C12M 33/14; C12P 19/02

USPC .................................................... 435/292.1
See application file for complete search history.

(56) References Cited

U.S. PATENT DOCUMENTS

| | | | | |
|---|---|---|---|---|
| 5,856,174 A | * | 1/1999 | Lipshutz | B01F 11/0071 422/68.1 |
| 2006/0205085 A1 | * | 9/2006 | Handique | B01L 3/502707 436/177 |
| 2011/0183312 A1 | * | 7/2011 | Huang | C12M 23/12 435/3 |

* cited by examiner

*Primary Examiner* — Michael L Hobbs
(74) *Attorney, Agent, or Firm* — Lin & Associates Intellectual Property, Inc.

(57) ABSTRACT

A photosynthetic device includes a main body defining a microfluid chamber for causing photosynthesis therein, and a light source, wherein the microfluid chamber is constituted by at least one communication room, a plurality of micro channels respectively and spatially communicated with the communication room, at least one micro injection duct spatially communicated with the communication room, and a plurality of filter plugs spatially connected to the micro channels respectively and the micro injection duct at free ends thereof in order to filter fluid backflow in the micro channels and the micro injection duct. The light source radiates ceaselessly one of the communication room, the plurality of micro channels and the micro injection duct. The photosynthesis is resulted once chloroplasts and normal saline solution are injected into one of the communication room, the plurality of micro channels and the micro injection duct.

4 Claims, 2 Drawing Sheets

PHOTOSYNTHETIC DEVICE WITH MICROFLUID CHAMBER FOR CAUSING PHOTOSYNTHESIS THEREIN AND METHOD THEREOF

CROSS REFERENCE TO RELATED APPLICATIONS

This application is a Divisional of co-pending application Ser. No. 14/602,450, filed on Jan. 22, 2015, which is incorporated herewith by reference.

BACKGROUND OF THE INVENTION

1. Field of the Invention

The present invention relates generally to photosynthesis, more particularly to a photosynthetic device with a microfluid chamber and a method for causing photosynthesis in the microfluid chamber.

2. The Prior Arts

Owing to increase in concentration of so-called greenhouse gases (like carbon dioxide ($CO_2$), methan ($CH_4$) and nitrous oxide ($N_2O$)) produced by human activity and industry results in rising of the global temperature, which in turn, causes an increase evapotranspiration, thereby altering the heat balance system and changing the distribution of rainfall. That is causing the rainfall or floods in areas of drought originally, and the floods or rainfall in places where there is drought originally. Regarding the production of food crops, not only the temperature changes, so does the crop seasons, which is in need of moisture can not get water and/or vice versa, leading to significantly reducing the world crop production.

In addition to causing climate change, water crisis, food scarcity also result due to interactive effects. According to the UN assessment of global land resources, nearly a quarter of the world's agricultural land is affected or degraded seriously, but the world's population continues to grow. In order to feed all of humanity sufficiently, an increase of 70 percent of food production should be increased by 2050 the latest year or else starvation will be prevalent in the near future.

As such, the real solution for the currently existing problems resides in how to solve the food shortage and how to effectively reduce emission of greenhouse gases lie ahead of us.

SUMMARY OF THE INVENTION

A primary objective of the present invention is to provide a photosynthetic device with a microfluid chamber for causing photosynthesis in the microfluid chamber. The photosynthetic device of the present invention includes a main body defining a microfluid chamber 100 for causing photosynthesis therein, and a light source, wherein the microfluid chamber is constituted by: at least one communication room, a plurality of micro channels respectively and spatially communicated with the communication room, at least one micro injection duct spatially communicated with the communication room, and a plurality of filter plugs spatially connected to the micro channels respectively and the micro injection duct at free ends thereof in order to filter fluid backflow in the micro channels and the micro injection duct. The light source radiates ceaselessly one of the communication room, the plurality of micro channels and the micro injection duct. The photosynthesis is resulted once chloroplasts and normal saline solution are injected into one of the communication room, the plurality of micro channels and the micro injection duct.

In the present invention, the normal saline solution is injected ceaselessly into one of the communication room, the plurality of micro channels and the micro injection duct while the filter plugs prevent the chloroplasts from spilling out therefrom.

In this embodiment, the micro channels and the micro injection duct are rotatable relative to the communication room.

The photosynthetic device of the present invention further includes an extra communication room and a connection micro channel interconnecting spatially the extra communication room with the communication room. Preferably, the connection micro channel is rotatable relative to the extra communication room and the communication room.

Another objective of the present invention is to provide a method for causing photosynthesis via a photosynthetic device. The method accordingly includes the steps: injecting chloroplasts and normal saline solution into a micro channel; ceaselessly injecting chloroplasts and normal saline solution into the micro channel; and radiating the micro channel simultaneously in order to cause photosynthesis within the micro channel; wherein, the photosynthetic device includes a main body defining a microfluid chamber for causing photosynthesis therein, the microfluid chamber is constituted by a communication room, a plurality of the micro channels respectively and spatially communicated with the communication room, at least one micro injection duct spatially communicated with the communication room, and a plurality of filter plugs spatially connected to the micro channels respectively and the micro injection duct at free ends thereof in order to filter fluid backflow in the micro channels and the micro injection duct.

The photosynthetic device of the present invention further includes an extra communication room and a connection micro channel interconnecting spatially the extra communication room with the communication room. Preferably, the connection micro channel is rotatable relative to the extra communication room and the communication room.

In addition, the micro channels and the micro injection duct are rotatable relative to the communication room.

BRIEF DESCRIPTION OF THE DRAWINGS

The present invention will be apparent to those skilled in the art by reading the following detailed description of a preferred embodiment thereof, with reference to the attached drawings, in which.

DETAILED DESCRIPTION OF THE PREFERRED EMBODIMENT

The accompanying drawings are included to provide a further understanding of the invention, and are incorporated in and constitute a part of this specification. The drawings illustrate embodiments of the invention and, together with the description, serve to explain the principles of the invention.

Figure 1:
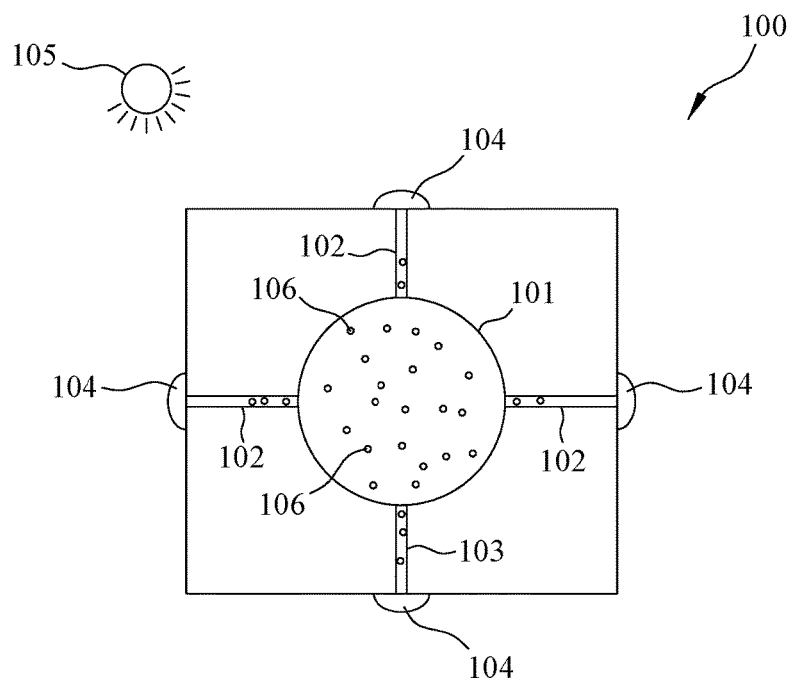
FIG. 1 is a schematic diagram illustrating the first embodiment of a photosynthetic device of the present invention.

FIG. 1 is a schematic diagram illustrating the first embodiment of a photosynthetic device of the present invention. The photosynthetic device of the present invention includes a main body 100 and a light source 105. The main body 100 defines a microfluid chamber for causing photosynthesis therein and preferably has a volume of 3.5 cm*3.5 cm*0.7 cm, but the size thereof should not be limited only thereto. The microfluid chamber is constituted by at least one communication room 101, a plurality of micro channels 102 respectively and spatially communicated with the communication room 101, at least one micro injection duct 103 spatially communicated with the communication room 101, and a plurality of filter plugs 104 spatially connected to the micro channels 102 respectively and the micro injection duct 103 at free ends thereof in order to filter fluid backflow in the aid micro channels 102 and the micro injection duct 103. The light source 105 is capable of radiating one of the communication room 101, the plurality of micro channels 102 and the micro injection duct 103. In this embodiment, the communication room 101, the micro channels 102 and the micro injection duct 103 are fabricated from transparent material, such as glass. The communication room 101 is circular in cross section and has a diameter of 2 cm, but the size should not be limited only thereto. Each of the micro channels 102 and the micro injection duct 103 has a first end connected spatially with the communication room 101 while the second ends of the micro channels 102 and the micro injection duct 103 are provided with the filter plugs 104 respectively such that photosynthesis is resulted once chloroplasts and normal saline solution are injected into one of the communication room 101, the micro channels 102 and the micro injection duct 103. Preferably, the micro channels 102 and the micro injection duct 103 are rotatable relative to the communication room 101 so as to evenly distribute the chloroplasts 106 within the channels and the injection duct in order to achieve the effective photosynthesis. Any connection means can be employed so long as it permits rotation of the micro channels 102 and the micro injection duct 103 relative to the communication room 101.

In this embodiment, the normal saline solution is injected ceaselessly into the communication room 101 and the micro channels 102 via the micro injection duct 103 while the filter plugs 104 prevent the chloroplasts from spilling out therefrom. Under this condition, chloroplasts within the normal saline solution are evenly and uniformly distributed so as to achieve the effective photosynthesis.

Figure 2:
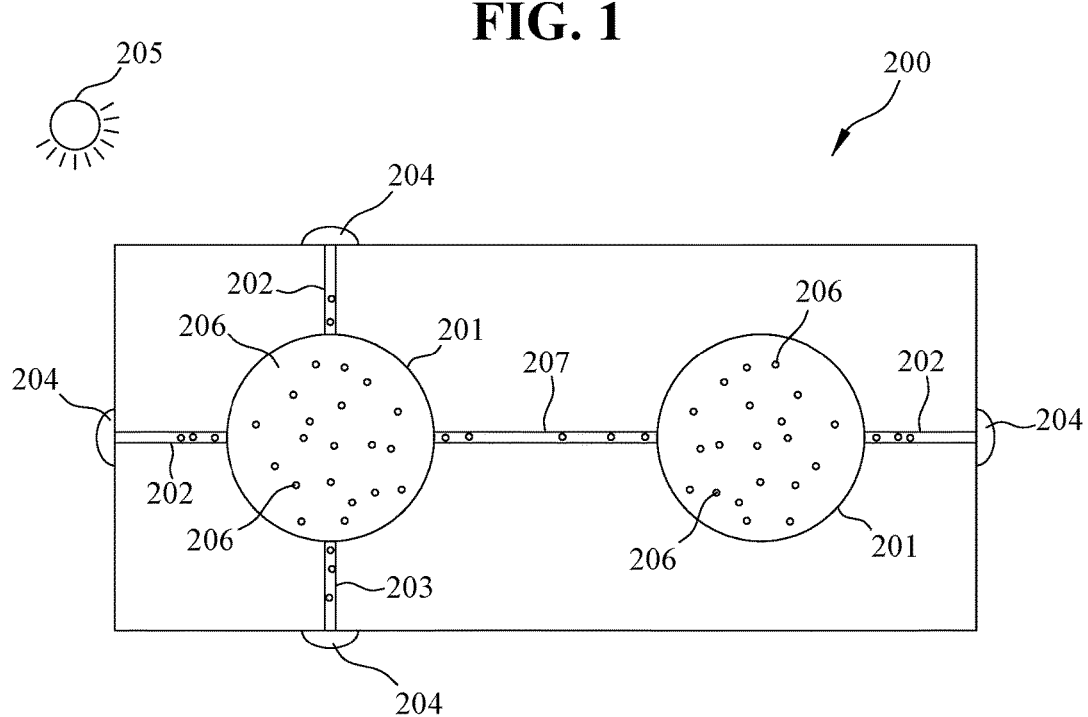
FIG. 2 is a schematic diagram illustrating the second embodiment of the photosynthetic device of the present invention.

FIG. 2 is a schematic diagram illustrating the second embodiment of the photosynthetic device of the present invention;

The second embodiment is generally identical to the first embodiment in structure, except in that the second embodiment of the photosynthetic device of the present invention further includes an extra communication room 201 and a connection micro channel 207 interconnecting spatially the extra communication room 201 with the communication room 201. Preferably, the connection micro channel 207 is rotatable relative to the extra communication room 201 and the communication room 201 so as to distribute the chloroplasts 206 evenly and uniformly within the connection micro channel 207 in order to achieve the effective photosynthesis once chloroplasts and normal saline solution are ceaselessly injected via the micro injection duct 203. Since mounting and functions of the filter plugs 204 are identical to the first embodiment, a detailed description thereof is omitted for the sake of brevity. An important to note is that only a single micro injection duct 203 is used in the second embodiment, however the number should not be limited only thereto.

Figure 3:
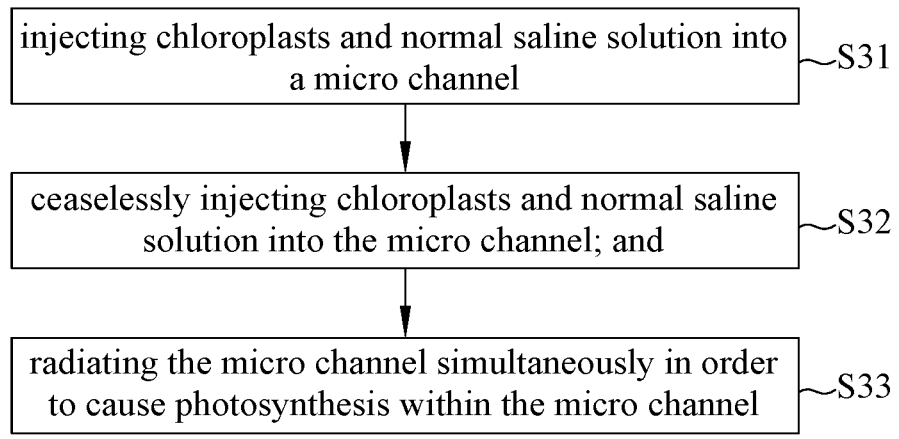
FIG. 3 shows a block diagram illustrating the steps constituting a method for causing photosynthesis via a photosynthetic device of the present invention.

FIG. 3 shows a block diagram illustrating the steps constituting a method for causing photosynthesis via a photosynthetic device of the present invention.

The method for causing photosynthesis via a photosynthetic device, wherein, the photosynthetic device includes a main body defining a microfluid chamber for causing photosynthesis therein. The method accordingly includes the steps: S31 injecting chloroplasts and normal saline solution into a microfluid chamber for causing photosynthesis therein, the microfluid chamber is constituted by a communication room 202, a plurality of the micro channels 202 respectively and spatially communicated with the communication room 201, at least one micro injection duct 203 spatially communicated with the communication room 201, and a plurality of filter plugs 204 spatially connected to the micro channels 202 respectively and the micro injection duct 203 at free ends thereof in order to filter fluid backflow in the micro channels 202 and the micro injection duct 203. Preferably, the micro channels 102 and the micro injection duct 103 are rotatable relative to the communication room 101. In step S32, chloroplasts and normal saline solution are injected ceaselessly via the micro injection duct. In step S33, one of the micro channels is radiated by a light source (such as sunlight) in order to cause photosynthesis within the micro channel.

Figure 4:
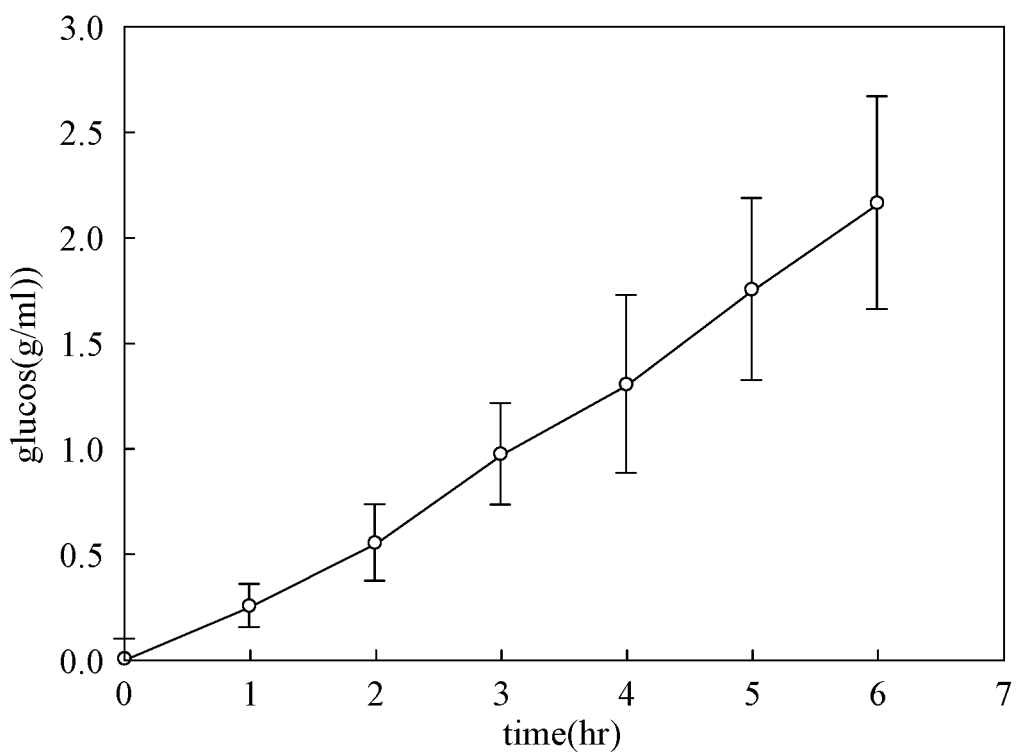
FIG. 4 is a graph illustrating the relation between glucose amount vs photosynthesizing time carried out according to the photosynthesizing method of the present invention.

FIG. 4 is a graph illustrating the relation between glucose amount vs photosynthesizing time carried out according to the photosynthesizing method of the present invention.

As illustrated in FIG. 1, since the normal saline solution is injected ceaselessly into the communication room 101 and the micro channels 102 via the micro injection duct 103 so as to cause photosynthesis therein and after reaction glucose spills out from the filter plugs 104. As shown in FIG. 4, after one hour of photosynthesis, 0.25 g/ml of glucose is obtained. After two hours of photosynthesis, 0.5 g/ml of glucose is obtained while 2.0 g/m1 of glucose is obtained after 6 hours of photosynthesis.

One aspect to note is that the photosynthesis is caused not in the green plant, but rather in the micro fluid chamber of the present invention as long as we can extract chloroplasts from plants and using the same in the photosynthetic device of the present invention so as to produce the glucose in combination with water and sunlight. In other words, emission of carbon dioxide can be reduced when the photosynthetic device of the present invention is implemented.

Although the present invention has been described with reference to the preferred embodiments thereof, it is apparent to those skilled in the art that a variety of modifications and changes may be made without departing from the scope of the present invention which is intended to be defined by the appended claims.

What is claimed is:

1. A method for causing photosynthesis via a photosynthetic device comprising the steps:
    injecting chloroplasts and normal saline solution into a micro channel;
    ceaselessly injecting chloroplasts and normal saline solution into said micro channel; and
    radiating said micro channel simultaneously in order to cause photosynthesis within said micro channel;
    wherein, the photosynthetic device includes a main body defining a microfluid chamber for causing photosynthesis therein, said microfluid chamber is constituted by a communication room, a plurality of said micro channels respectively and spatially communicated with said communication room, at least one micro injection duct spatially communicated with said communication room, and a plurality of filter plugs spatially connected to said micro channels respectively and said micro injection duct at free ends thereof in order to filter fluid backflow in said micro channels and said micro injection duct.

2. The method according to claim 1, wherein the photosynthetic device further includes a light source for radiating ceaselessly to one of said communication room, said plurality of micro channels and said micro injection duct, an extra communication room and a connection micro channel interconnecting spatially said extra communication room with said communication room.

3. The method according to claim 2, wherein said connection micro channel is rotatable relative to said extra communication room and said communication room.

4. The method according to claim 1, wherein said micro channels and said micro injection duct are rotatable relative to said communication room.

\* \* \* \* \*